(12) United States Patent
De Lurgio et al.

(10) Patent No.: US 6,714,823 B1
(45) Date of Patent: Mar. 30, 2004

(54) CARDIAC PACING LEAD AND DELIVERY SYSTEM

(75) Inventors: David B. De Lurgio, Atlanta, GA (US); Jonathan J. Langberg, Atlanta, GA (US)

(73) Assignee: Emory University, Atlanta, GA (US)

( * ) Notice: Subject to any disclaimer, the term of this patent is extended or adjusted under 35 U.S.C. 154(b) by 173 days.

(21) Appl. No.: 09/693,569

(22) Filed: Oct. 20, 2000

Related U.S. Application Data (63) Continuation of application No. PCT/US99/09427, filed on Apr. 28, 1999.
(60) Provisional application No. 60/083,448, filed on Apr. 29, 1998.

(51) Int. Cl.[7] .................................................. A61N 1/05
(52) U.S. Cl. ........................ 607/122; 607/119; 600/585
(58) Field of Search .............................. 607/116, 119, 607/122, 125, 127, 123; 600/585, 374, 373; 128/899

(56) References Cited

U.S. PATENT DOCUMENTS

| | | | |
|---|---|---|---|
| 3,333,045 A | | 7/1967 | Fisher et al. |
| 4,281,668 A | | 8/1981 | Richter et al. |
| 4,311,153 A | * | 1/1982 | Smits .......................... 607/127 |
| 4,483,577 A | | 11/1984 | Novis |
| 4,748,986 A | * | 6/1988 | Morrison et al. ........... 600/585 |
| 4,750,494 A | | 6/1988 | King |
| 4,895,168 A | * | 1/1990 | Machek ...................... 600/585 |
| 4,922,927 A | | 5/1990 | Fine et al. |
| 4,928,688 A | | 5/1990 | Mower |
| 4,957,110 A | * | 9/1990 | Vogel et al. ................ 600/381 |
| 4,966,599 A | | 10/1990 | Pollock |
| 5,099,838 A | | 3/1992 | Bardy |
| 5,165,403 A | | 11/1992 | Mehra |
| 5,261,417 A | * | 11/1993 | Osypka ....................... 607/127 |

(List continued on next page.)

FOREIGN PATENT DOCUMENTS

| | | |
|---|---|---|
| GB | 2248201 | 8/1991 |
| GB | 2248201 A | 8/1991 |
| WO | WO 99/55412 | 11/1999 |

OTHER PUBLICATIONS

The Annals of Thoracic Surgery, "Acute Hemodynamic Effects of Atrio–Biventricular Pacing in Humans," Andrew H. Foster MD; Michael R. Gold, MD, PhD; and Joseph S. McLaughlin, MD; pp. 294–300, vol. 59, No. 2, Feb. 1995.
The Annals of Thoracic Surgery, "Correspondence," pp. 1156–1162, vol. 60, No. 4, Oct. 1995.
Artificial Electric Cardian Stimulation; Chapter 1 "Artificial Electric Cardiac Stimulation" Kenneth B. Stokes; G. Neal Kay.

(List continued on next page.)

*Primary Examiner*—Kennedy Schaetzle
(74) *Attorney, Agent, or Firm*—John P. O'Banion

(57) ABSTRACT

A pacing lead that is useful for transvenous pacing of the left ventricle, particularly in patients with congestive heart failure. The pacing lead includes a tapered body of reduced diameter at its distal end, and at least one electrode positioned in the area of the thin distal end of the tapering body. A floppy coil is attached as an integral part of the tapered body, or provided as a separate component, to serve as a guidewire for steering the pacing lead. Also provided with is a sheath delivery system for delivery of the pacing lead into the coronary sinus or a distal cardiac vein. The delivery system includes a J-tipped guidewire insertable into the right atrium or right ventricle from a cephalic or subclavian vein, a sheath with preformed curve, and a dilator, wherein the sheath, with the dilator positioned therein, is advancable over the guidewire placed into the right ventricle, the guidewire and dilator thereafter removable to cannulate the ostium of the coronary sinus or a distal cardiac vein, and provide guidance for a pacing lead advancable through the sheath into the coronary sinus.

30 Claims, 5 Drawing Sheets

U.S. PATENT DOCUMENTS

| | | | |
|---|---|---|---|
| 5,269,319 A | | 12/1993 | Schulte et al. |
| 5,466,254 A | | 11/1995 | Helland |
| 5,476,498 A | * | 12/1995 | Ayers .......................... 607/122 |
| 5,509,411 A | * | 4/1996 | Littmann et al. ........... 600/381 |
| 5,531,781 A | * | 7/1996 | Alferness et al. ........... 607/122 |
| 5,545,204 A | * | 8/1996 | Cammilli et al. ........... 607/123 |
| 5,639,276 A | | 6/1997 | Weinstock et al. |
| 5,674,273 A | | 10/1997 | Helland |
| 5,755,766 A | * | 5/1998 | Chastain et al. ............ 607/122 |
| 5,803,928 A | * | 9/1998 | Tockman et al. ........... 607/122 |
| 5,935,160 A | | 8/1999 | Auricchio et al. |
| 5,971,983 A | * | 10/1999 | Lesh ........................... 606/41 |
| 6,138,043 A | * | 10/2000 | Avitall ........................ 600/377 |

OTHER PUBLICATIONS

Artificial Electric Cardiac Stimulation; Chapter 3 "Engineering and Clinical Aspects of Pacing Leads" Harry G. Mond; John R. Helland.

Artificial Electric Cardiac Stimulation; Chapter 23 "Basic Physiology of Cardiac Pacing" Denise L. Janosik; Arthur J. Labovitz.

Artificial Electric Cardiac Stimulation Chapter 30 "Pacemaker Radiography" Lon W. Castle; Sebastian Cook.

Pace; "Permanent Ventricular Pacing Via the Great Cardiac Vein," Yuping Bai; Neil Strathmore; Harry Mond; Leeanne Grigg; and David Hunt; pp. 768–683, vol. 17, No. 4, Part II, Apr. 1994.

Pace; "Four Chamber Pacing in Dilated Cardiomyopathy," S. Cazeau; P. Ritter; S. Bakdach; A. Lazarus; M. Limousin; L. Henao; O. Mundler; J.C. Daubert; and J. Mugica; pp. 1974–1979, vol. 17, No. 11, Part II, Nov. 1994.

Pace; "Successful Long–Term Ventricular Pacing Via the Coronary Sinus After Fontan Operation" Eric Rosenthal; Shakeel A. Qureshi; and Jonathan C. Pitts Crick, pp. 2103–2105, vol. 18, No. 11, Nov. 1995.

NASPE Abstracts; "Beneficial Effects of Biventricular Pacing in Congestive Heart Failure," Patricia F. Bakker, MD; Huub Meijburg, MD; Nicolaas de Jonge, MD; Rob van MEchelen, MD; Fred Wittkampf, Ph.D.; Morton Mower, MD; and Andra Thomas, RN; p. 820; vol. 17, Part II, Apr. 1994.

Pace; "Multisite Pacing for End–Stage Heart Failure: Early Experience," Serge Cazeau; Philippe Ritter; Arnaud Lazarus; Daniel Gras; Hayssam Backdach; Oliver Mudler; and Jacques Mugica, pp. 1748–1757, vol. 19, Part II, Nov. 1996.

The American Journal of Cardiology; "Evaluation of End Points of Serial Drug Testing in Patients with Sustained Ventricular Tachcardia After Healing of Acute Myocardial Infarction," Stan J. Wasilewski, MD; Kevin J. Ferrick, MD; James A. Roth, MD: Soo G. Kim, MD; and John D. Fisher, MD; pp. 1247–1252, vol. 76, Dec. 15, 1995.

Design of Cardiac Pacemarkers; Edited by John G. Webster; "Electrodes, Leads, and Biocompatibility," Brian K. Wagner; Chapter 6, pp. 132–160, IEEE Engineering in Medicine and Biology Society, (1993).

Journal of American College of Cardiology; "Mechanism of Hemodynamic Improvement by Dual–Chamber Pacing for Severe Left Ventricular Dysfunction: An Acute Doppler and Catherization Hemodynamic Study," Rick A. Nishimura, MD; David L. Hayes, MD: David R. Holmes, Jr., MD; A. Jamil Tajik, MD; pp. 281–288, vol. 25, No. 2, Feb. 1995.

Blackburn, M.E. C.; Gibbs, J.L., "Ventricular Pacing from the Coronary Sinus of a Patient with a Fontan Circulation," British Heart Journal; vol. 70; 1993, pp. 578–579.

Lemery, Robert, et al., "Results of a Comparative Study of Low Energy Direct Current with Radiofrequency Ablation in Patients with the Wolff–Parkinson–White Syndrome," British Heart Journal; vol. 70; 1993, pp. 580–584.

Parry, G.W., et al., "Antibiotic Prophylaxis for Cardiac Surgery: Current United Kingdom Practice," British Heart Journal; vol. 70; 1993, pp. 585–586.

Hollman, Arthur, "How John Parkinson Did the Post Mortem on Sir James MacKenzie," British Heart Journal; vol. 70; 1993, pp. 587–590.

Stokes, Kenneth B., G. Neal Kay; "Artificial Electric Cardiac Stimulation," Chapter 1, Artificial Electric Cardiac Stimulation, Date and Publisher unknown.

Mond, Harry G., Helland, John R.; Engineering and Clinical Aspects of Pacing Leads, Chapter 3, Artificial Electric Cardiac Stimulation, Date and Publisher unknown.

Janosik, Denise L., Labovitz, Arthur J.; "Basic Physiology of Cardiac Pacing," Chapter 23, Artificial Electric Cardiac Stimulation, Date and Publisher unknown.

Castle, Lon W., Cook, Sebastian; "Pacemaker Radiography," Chapter 30, Artificial Electric Cardiac Stimulation, Date and Publisher unknown.

Bai, Y., et al.; "Permanent Ventricular Pacing Via the Great Cardiac Vein," Pacing and Clinical Electrophysiology, vol. 17, No. 4, Part II, Apr., 1994, pp. 709–871.

Cazeau, S., et al.; "Four Chamber Pacing in Dilated Cardiomyopathy," Pacing and Clinical Electrophysiology, vol. 17, No. 11, Part II, Nov., 1994, pp. 1837–2227.

Rosenthal, E., et al.; "Successful Long–Term Ventricular Pacing via the Coronary Sinus After the Fontan Operation," Pacing and Clinical Electrophysiology, vol. 18, No. 11, Nov., 1995, pp. 1977–2108.

Bakker, Patricia, F., et al.; "Beneficial Effects of Biventricular Pacing in Congestive Heart Failure," NASPE Abstracts, Pacing and Clinical Electrophysiology, vol. 17, No. 11, Part II, Apr., 1994, pp. 820.

Cazeau, S., et al.; "Multisite Pacing for End–Stage Heart Failure: Early Experience," Pacing and Clinical Electrophysiology, vol. 19, Part II, Nov., 1996, pp. 1748–1757.

Wasilewski, Stan J., et al.; "Evaluation of End Points of Serial Drug Testing in Patients with Sustained Ventricular Tachycardia Healing of Acute Myocardial Infarction," Amer. J. of Cardiology, vol. 76, Dec. 15, 1995, pp. 1247–1252.

Wagner, Brian K.; "Electrodes, Leads and Biocompatibility," (ed) Webster, John G.; Design of Cardiac Pacemakers, IEEE Engineering in Medicine and Biology Society, 1995, pp. 133–160.

Nishimura, Rick A. et al.; Mechanism of Hemodynamic Improvement by Dual–Chamber Pacing for Severe Left Ventricular Dysfunction: An Acute Doppler and Catheterization Hemodynamic Study, JACC, vol. 25, No. 2, Feb., 1995, pp. 281–288.

Foster, Andrew H., et al.; Acute Hemodynamic Effects of Atrio–Biventricular Pacing in Humans, Annals of Thoracic Surgery, vol. 59, No. 2, Feb., 1995, pp. 294–300.

Broka, Serge, et al.; Correspondence, Hemodynamic Effects of Atrio–Biventricular Pacing In Humans, Annals of Thoracic Surgery, vol. 60, No. 4, Oct., 1995, pp. 1155–1162.

* cited by examiner

CARDIAC PACING LEAD AND DELIVERY SYSTEM

CROSS-REFERENCE TO RELATED APPLICATIONS

This application is a continuation of PCT/US99/09427 filed Apr. 28, 1998, which claims priority from U.S. provisional application Ser. No. 60/083,448 filed on Apr. 29, 1998.

BACKGROUND OF THE INVENTION

1. Field of the Invention

The present invention pertains generally to medical devices for cardiac pacing, and more particularly to a pacing lead and associated sheath delivery system. The pacing lead has a tapering body with a thin distal lead shaft and at least one electrode in a configuration that permits increased steerability to enable permanent transvenous pacing of the left ventricle of the heart.

2. Description of the Background Art

The heart, which is an essential organ in the body, rhythmically pumps blood throughout the body so as to supply oxygen and energy to cells. The inability of the heart to maintain proper rhythm, however, can lead to congestive heart failure in which blood backs up into the lungs and/or veins.

Congestive heart failure is a major cause of morbidity and mortality worldwide, with over 350,000 heart failure deaths each year in the United States alone. At any one time an even greater number of Americans are living with advanced congestive heart failure. These numbers are expected to grow as our population continues to age and a larger proportion of Americans are in the older age groups.

Patients with advanced heart failure have markedly increased mortality (20% to 40% per year). In such cases, treatment involves multiple medications. For younger, otherwise healthy heart failure patients, heart transplantation is often considered. Unfortunately, the restricted supply of donor hearts, as well as side effects related to immunosuppressive therapy, severely limit the widespread applicability of this surgical procedure. Therefore, many people will suffer and die with intractable congestive heart failure.

It is well known that pacemakers can be used to reestablish normal cardiac rhythms. A pacemaker consists of two parts: a pulse generator, and an attached lead or leads. The lead includes at least one insulated wire with an attached electrode that transmits an electrical pulse from the pulse generator to the cardiac tissue. Receipt of the output pulse causes depolarization and contraction of cardiac tissue, in a phenomenon termed "capture."

Most pacemakers operate on demand, so that the output pulse is generated in response to a signal from the lead, which continuously monitors or senses the intrinsic electrical activity of the heart. In contrast, asynchronous pacemakers deliver electrical impulses to the cardiac tissue at a fixed rate.

Pacemakers are commonly implanted in a minor surgical procedure during which the patient is mildly sedated and given a local anesthetic. Through an incision near the collar bone, the pulse generator is implanted under the skin and the leads are inserted into a vein leading to the heart. The leads are then advanced to the heart using continuous fluoroscopic guidance. The electrode is then positioned or fixed within the heart. A lead passed through a vein for fixation within the heart is termed transvenous. Once positioned, the leads are generally not removed.

There are two types of pacemakers: single-chamber, and dual-chamber. Single-chamber pacemakers typically have one lead positioned within the right atrium or right ventricle. Dual-chamber pacemakers (DDD) on the other hand typically have two leads, one positioned within the right atrium and one positioned within the right ventricle.

It has recently been observed that specialized pacing modalities may reduce symptoms and improve the quality of life in patients with advanced heart failure. DDD pacing with shortened atrioventricular (AV) delay is efficacious in patients with endstage idiopathic dilated cardiomyopathy. A symptomatic improvement has been observed, as well as improvement in left ventricular ejection fraction. Other observations include clinical and hemodynamic improvement with shortened AV delay pacing.

Typically, the leads of a dual-chamber pacemaker are placed within the right side of the heart. Under several circumstances, however, simultaneous pacing of both the right and the left ventricle may be desirable. Pacing both ventricles may simultaneously result in a dramatic improvement in clinical status and ventricular function in patients with congestive heart failure. In other circumstances, the right ventricle cannot be safely accessed, and transvenous pacing of the left ventricle may be a desirable substitute. Though rare, access to the right ventricle may be limited because of tricuspid valve stenosis, the presence of a tricuspid valve prosthesis, a congenital heart defect, or as the result of certain surgical procedures.

While left ventricular transvenous pacing is clearly desirable, it is presently unavailable. Left ventricular pacing, on the other hand, is limited to epicardial leads. In one known study, for example, a standard permanent pacing lead was implanted in the right ventricular apex and utilized an epicardial lead for the left ventricle. In contrast to a transvenous lead, an epicardial lead is attached to the outside of the heart, by known fixation methods. Placement of an epicardial lead requires that the surface of the heart be exposed, for example by thoracatomy, and involves considerable operative risk in these already very sick patients.

Currently there are no devices for permanent transvenous left ventricular pacing. Limitations and difficulties in carrying out such pacing include access to the distal cardiac veins, attainment of adequate pacing capture thresholds, and prevention of pacing lead dislodgment. A device designed for such pacing must overcome these obstacles and be simple to use. The device must allow the operator to easily cannulate the orifice of, for example, the coronary sinus. Furthermore, the pacing lead must be designed to allow advancement into selected distal veins at the discretion of the operator. A low profile device is required for cannulation of veins with diameters as small as 1.5 mm or less. Also, the pacing lead must be designed to prevent dislodgment once the desired pacing site has been selected.

BRIEF SUMMARY OF THE INVENTION

The present invention satisfies the foregoing needs, as well as others, and overcomes deficiencies associated with prior devices, thus providing a permanent pacing lead that is useful for transvenous pacing of the left ventricle, particularly in patients with congestive heart failure. In general terms, the present invention pertains to an apparatus and method for permanent cardiac pacing in the distal cardiac veins, particularly the coronary sinus of the left ventricle. The invention is designed to provide a safe, effective, and practical tool for such cardiac pacing.

By way of example, and not of limitation, a device for left ventricular pacing via the distal cardiac veins according to the invention comprises a tapered body of reduced diameter at its distal end, and at least one electrode positioned in the area of the thin distal end of the tapering body. A floppy coil can be attached as an integral part of the tapered body, or provided as a separate component, to serve as a guidewire for steering the pacing lead. Notably, the invention does not include means for securing the distal end thereof to the wall of the heart after placement.

In a first embodiment of the invention, a floppy coil is affixed to the distal end of the pacing lead as a guidewire. A conventional stylet is inserted into the pacing lead for steering, but does not extend into the floppy coil. Here, the floppy coil remains after placement of the pacing lead since it is an integral part of the pacing lead.

In an alternative embodiment of the invention, an integral floppy coil is not provided. Instead, a stylet with a floppy coil at its distal end is provided for steering. In this embodiment of the invention, the tapered body includes a central lumen and a water-tight valve with a central entrance coaxial to the central lumen. The distal end of the coil, and eventually the stylet, is inserted into the proximal end of the tapered body until the coil extends through the center of the water-tight valve and out the distal end of the body. The amount of protrusion can be adjusted to the desired length. The coil is then used as a guidewire to position the pacing lead. When the coil is in position, the stylet/coil assembly can be withdrawn to leave the pacing lead in position. Note, however, that this embodiment also permits "over the wire" positioning. In other words, the pacing lead can be moved distally over the coil until the distal end of the pacing lead is in any position along the coil. After placement of the pacing lead, the stylet/coil assembly is retracted. In either placement approach, the valve automatically closes off to make a watertight seal when the stylet/coil assembly is withdrawn.

In accordance with one electrode configuration of the invention, the device comprises a bipolar pacing lead with both a proximal ring electrode and a distal ring electrode, wherein the electrodes each form a cylinder configuration having about 1 mm in height.

In accordance with an alternative electrode configuration of the invention the device comprises a unipolar pacing lead with a distal electrode at or near the distal terminus of the tapering body, wherein the electrode forms a cylinder configuration having about 1 mm in height.

Also provided with the invention is a sheath delivery system for delivery of the pacing lead into the coronary sinus or a distal cardiac vein. Such a delivery system comprises a J-tipped guidewire insertable into the right atrium or right ventricle from a cephalic or subclavian vein, a sheath with preformed curve, and a dilator, wherein the sheath, with the dilator positioned therein, is advancable over the guidewire placed into the right ventricle, the guidewire and dilator thereafter removable to cannulate the ostium of the coronary sinus or a distal cardiac vein, and provide guidance for a pacing lead advancable through the sheath into the coronary sinus.

An object of the invention is to provide a safe, effective, and practical tool for permanent cardiac pacing in the distal cardiac veins.

Another object of the invention to provide means for transvenous ventricular pacing in patients who require cardiac pacing but without transvenous access to the right ventricle.

Another object of the invention is to provide a pacing system which can be used in conjunction with standard pacing leads to transvenously pace the left ventricle synchronously with the right ventricle. Such synchronous pacing is particularly advantageous for patients with congestive heart failure due to idiopathic dilated cardiomyopathy or dilated cardiomyopathy from advanced heart disease.

Another object of the invention is to replace a standard ventricular pacing lead in any patient requiring ventricular pacing.

Another object of the invention is to provide a permanent pacing lead that is useful for transvenous pacing of the left ventricle, particularly in patients with congestive heart failure.

Another object of the invention is to Applicants provide a novel design and method for a pacing lead system that allows permanent transvenous pacing of the left ventricle without opening the chest.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 1 through FIG. 11 and the method of use described in connection therewith. It will be appreciated that the apparatus may vary as to configuration and as to details of the parts, and that the method may vary as to details of steps and their sequence, without departing from the basic concepts as disclosed herein.

Figure 1:
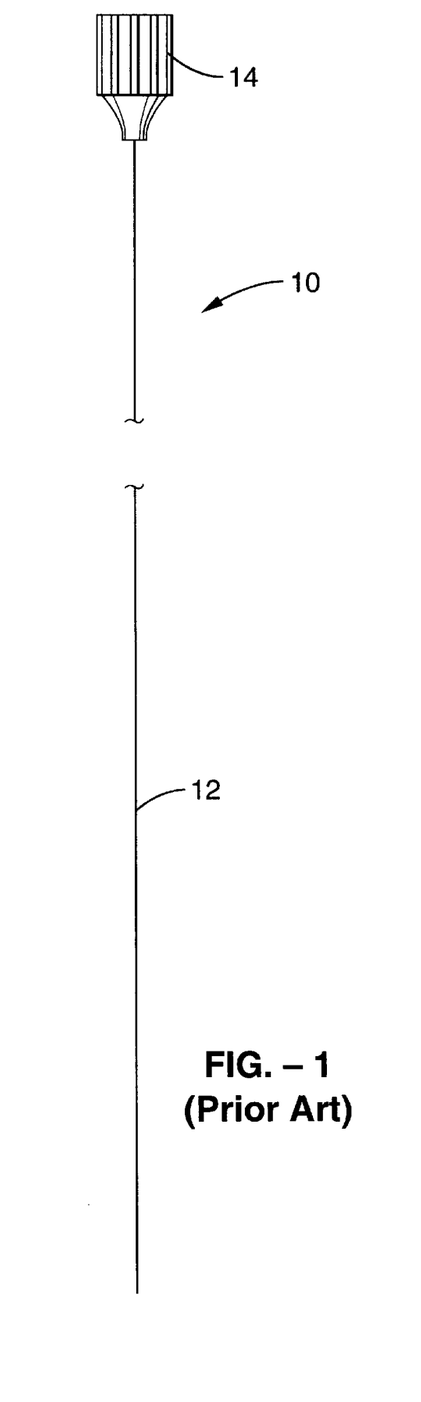
FIG. 1 is a side elevation of a conventional stylet used when placing pacing leads.

The present invention provides a pacemaker lead suitable for transvenous pacing, particularly the coronary sinus of the left ventricle. The pacemaker lead of the present invention is substantially modified as compared to conventional leads to increase maneuverability or steerability thereof by the surgeon during placement within the heart. Referring first to FIG. 1, in a conventional pacing lead a stylet 10 comprising a stiff wire 12 and associated safety hub 14 is inserted into a lumen for steering. The lumen typically exists in the distal portion of the pacing lead and the stylet does not extend beyond the tip of the pacing lead. When the pacing lead is in position, the stylet is withdrawn. While this pacing lead configuration and placement methodology is suitable for many pacing applications, it is not suitable for placement in transvenous locations such as the great coronary vein or coronary sinus of the left ventricle. Nor is a conventional pacing lead tapered so as to have a thinner distal end in relation to the proximal end. Furthermore, once the stylet is removed, it cannot be reinserted if it is necessary to reposition the pacing lead.

In contrast, the basic structure of the pacing lead of the present invention is that of a tapering body with a thin distal lead shaft. The lead includes at least one insulated wire, or conductor, with an attached electrode. The lead wire can be straight or coiled, and a given lead can have one or more lead wires. The use and attachment of lead wires to electrodes is well known in the art and, therefore, not described herein.

Notably, the pacing lead tip of the present invention lacks attachment means for securing the pacing lead tip to the wall of the heart after placement by the surgeon. Conventional pacing leads typically require such attachment means. For example, standard pacing leads have tines attached to their distal terminus, the tines (or prongs) usually made of silicone, having lengths of approximately 2 mm to approximately 3 mm. Another common feature of conventional pacing leads is a terminal helical screw made of metal, also sometimes serving as the distal electrode. These and other attachments means need not be incorporated into the present invention.

Figure 2:
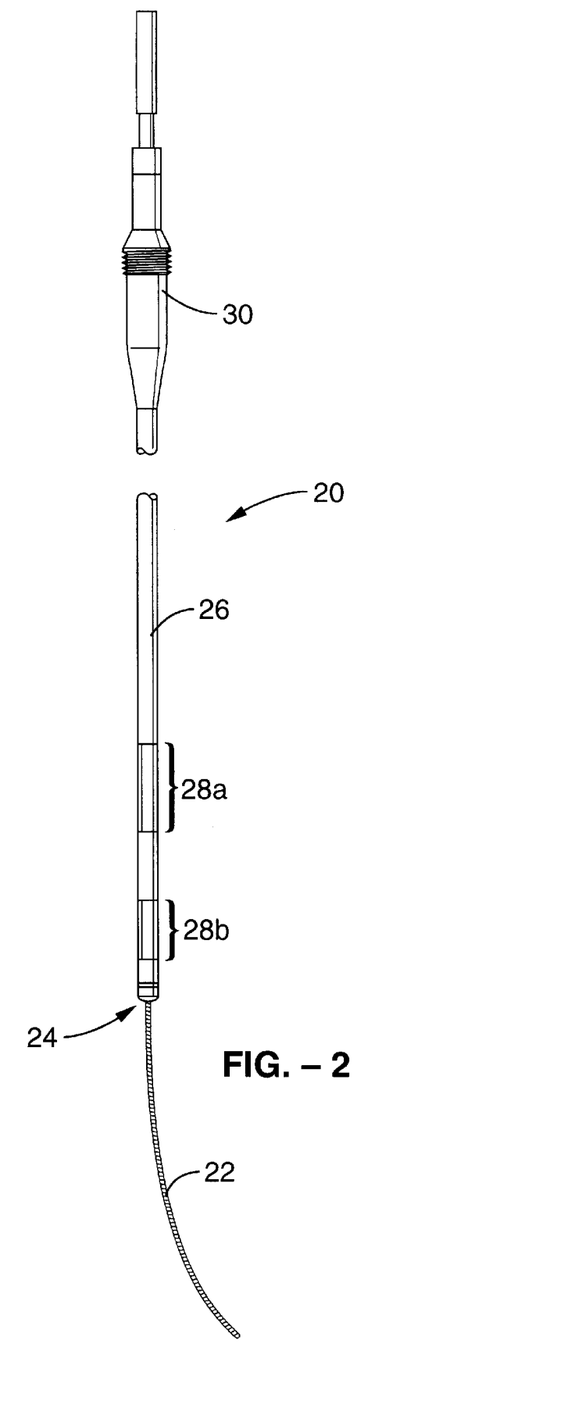
FIG. 2 is a side elevation of a pacing lead according to the present invention having a thin distal lead shaft, a bipolar electrode configuration, and a floppy, steerable coil attached to the distal end as a guidewire.

Referring now to FIG. 2, a pacing lead 20 according to the present invention is shown. Pacing lead 20 comprises a thin, floppy, steerable coil 22 affixed to the distal end 24 of a tapering body 26, bipolar electrodes 28a, 28b adjacent the thin distal end of the tapering body, and a conventional connector pin assembly 30 at the proximal end of the tapering body. Preferably the coil is floppy, having a hollow interior such as those used in connection with angioplasty. It is also possible, however, to use a coil that has a central wire but with an increased risk of endovascular trauma. With regard to the connector pin, those skilled in the art will appreciate that connector pins are commonly used as an interface between the electrode lead wires and the pacemaker header, and are will known in the art. In the present invention, the distance between the bipolar electrodes can vary typically between approximately 0.5 cm and approximately 3 cm, and preferably between approximately 1 cm and approximately 2 cm. The floppy steerable guidewire or coil is preferably formed of stainless steel, but could be formed of other materials. The remainder of the pacing lead is fabricated from materials which are commonly used in the fabrication of pacing leads.

Note that the diameter of the pacing lead itself is an important feature of the present invention. The thin diameter of the pacing lead permits cannulation of small caliber cardiac veins. Preferably the diameter of the distal lead shaft ranges from approximately 1 mm to approximately 3 mm. Small caliber distal cardiac veins may have diameters as small as about 1 mm to about 1.5 mm. In contrast, conventional bipolar pacing leads have diameters of about 3 mm, and the lead electrodes are often not flush with the lead shaft. Such defects in the design of conventional bipolar pacing leads makes them unsuitable for cannulation of small caliber cardiac veins.

The tapering body with a thin distal segment provides stiffness to the proximal portion of the lead shaft which is inserted into and rests in the great veins and right atrium. The increased stiffness allows pacing lead 20 to rest against the right atrial wall and transmit a small amount of force distally to the thin portion of the body, thereby reducing the risk of lead dislodgment.

Apart from having a thin diameter, a pacing lead for cannulation of the distal cardiac veins must be highly steerable. Hence, the steerable guidewire is also an important feature of the present invention. The guidewire, which is in the form of a coil as described above, is steered into the cardiac veins, thereby leading the way to distal pacing sites. According to the present invention, selective cannulation of the branches of the cardiac veins is conferred by a curved floppy coil that is can be rotatably positioned to allow faithful transmission of the torque applied at the proximal end of the pacing lead by the operator. The floppy design allows the operator to direct and re-direct the pacing lead tip as needed without the risk of endovascular trauma. Once a vein branch is selected, the coil allows the operator to advance the pacing lead distally, since the guidewire allows transmission of force along its long axis. To assist with steering, a stylet of the type shown in FIG. 1 can be inserted into a lumen (not shown) in body 26. If used, such a lumen would run down the center of the body between the proximal and distal ends thereof.

In the embodiments thus described the curved guidewire or coil is an integral component of the pacing lead. However, an attached coil is not a requirement of the invention. Referring to FIG. 3 through FIG. 6, an alternative embodiment 32 of the invention is shown where the distal coil is not fixed or attached to the end of the tapering body. Here, a hollow body 34 with a central channel or lumen 36 (FIG. 5) is used in conjunction with a water-tight self-closing grommet-type valve 38, which has an opened and a closed position is affixed to the of the hollow body. The central lumen extends between a proximal port P1 adjacent to the end of connector pin assembly 30 and a distal port P2 at the end of the body. In this regard, it will be appreciated that connector pin assembly 30 would be hollow in the configuration described. However, if the connector pin assembly is not hollow, a proximal port P1' would be located adjacent to the coupling point between connector pin assembly 30 and the lead body. Distal port P2 is coaxial with a pore or aperture 40 in valve 38 which is continuous with the central lumen 36. In the closed position, the central channel 36 is sealed. Valve 38 can be cylindrical in shape, or the proximal and/or distal edges can be beveled if desired.

Figure 5:
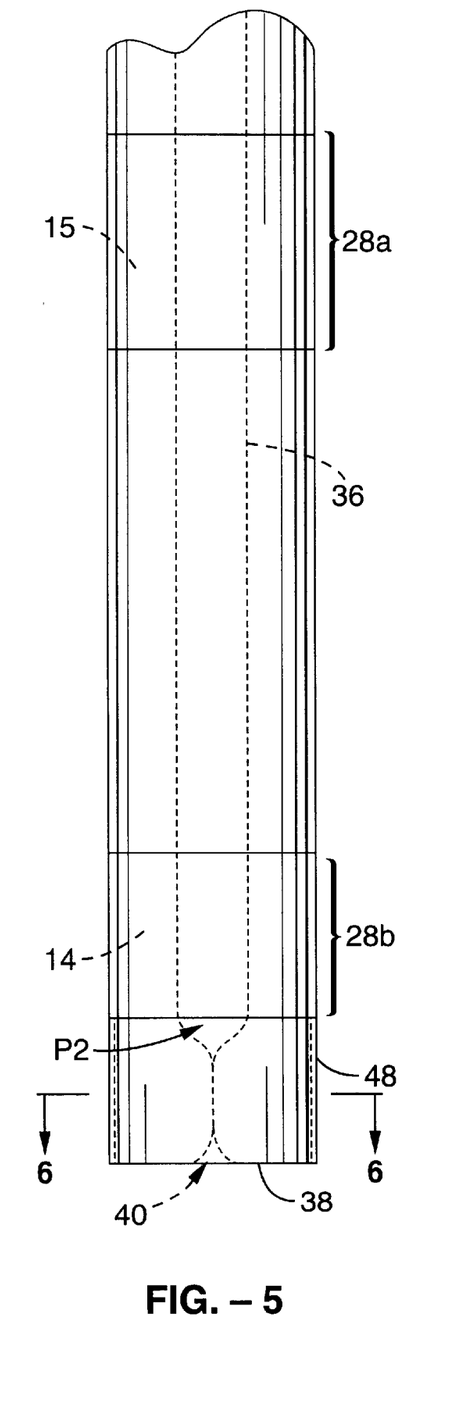
FIG. 5 is a fragmentary view, in side elevation, of the tip of the pacing lead shown in FIG. 3 with the water-tight valve shown in a closed position.
Figure 6:
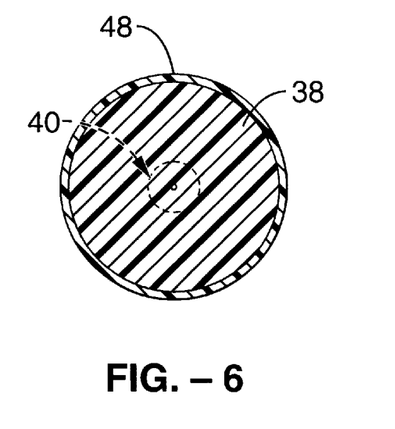
FIG. 6 is a cross-sectional view of the water-tight valve portion of the tip shown in FIG. 5 taken through line 6—6.

Valve 38 is preferably made of flexible, non-conductive, abrasion resistant materials of high lubricity, such as molded rubber or silastic rubber compositions. Other suitable materials for valve construction include, but are not limited to, silicone rubber and polyurethane. Silastic rubber is the most preferable because of increased elasticity allowing more readily the protrusion of the stylet with the formation of a water-tight seal after withdrawal of the coil. However, the valve can also be made of siloxane. The valve may be molded to the tip of the pacing lead to form a valve housing, which is continuous with the outer insulation of the pacing lead body.

Alternatively, the valve may be housed within a distal metallic ring which also serves as a distal pacing electrode. Or, a separate metallic ring on the distal tip of the pacing lead serves solely as the housing for the valve.

Figure 3:
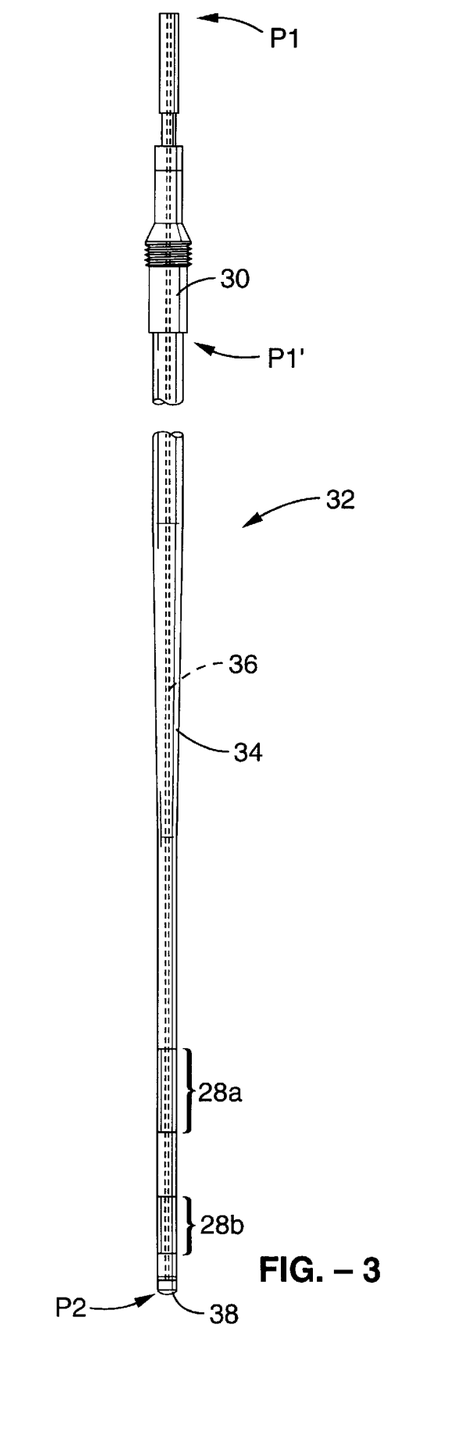
FIG. 3 is a side elevation of a pacing lead according to the present invention having a thin distal lead shaft and a bipolar electrode configuration, but without an attached steerable coil.
Figure 4:
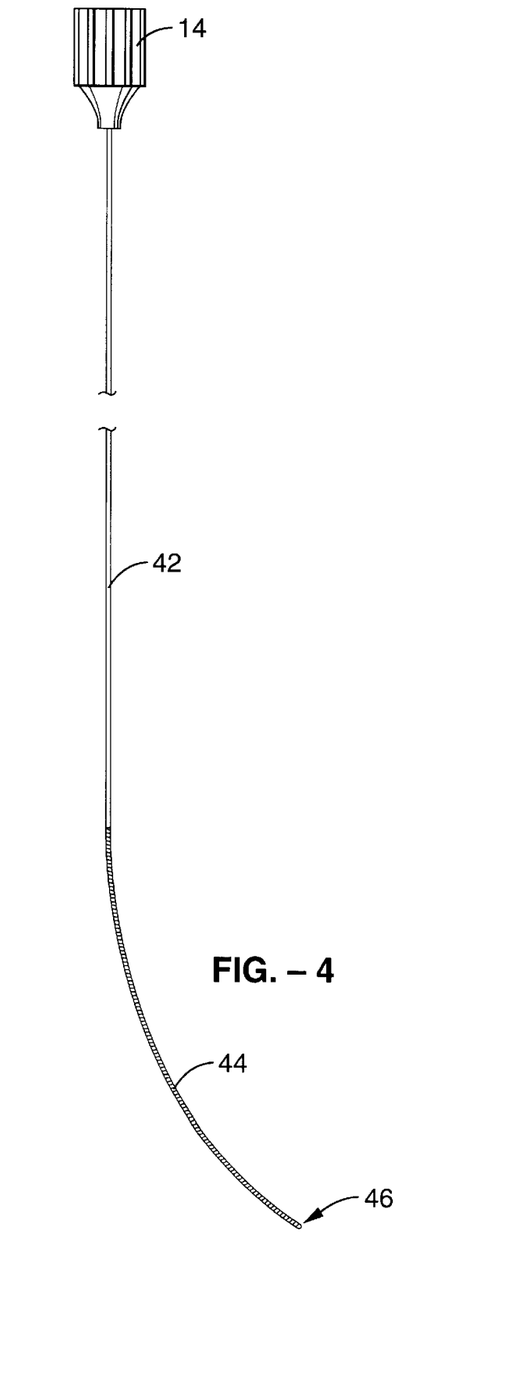
FIG. 4 is a side elevation of a floppy, steerable coil affixed to a conventional stylet for use in steering the pacing lead shown in FIG. 3.

As can be seen, in this embodiment of the invention the pacing lead 32 lacks an attached steerable coil. Instead, as shown in FIG. 4, a stylet 42 with a steerable distal floppy coil 44 is provided for insertion and removal from the central lumen of body 34. The central channel 36 provides a lumen for inserting the stylet and coil for positioning the pacing lead. Suitable stylets for cannulation of small caliber veins include, but are not limited to, stylets with or without distal floppy coils, having the appropriate design. If desired, coil 44 can include a blunt tip 46.

Stylet 42 is typically attached to the distal floppy coil 44 by welding or other conventional attachment techniques. Suitable materials for both the stylet and the distal floppy coil are high-torque stainless steel.

The stylet 42, with its attached coil 44, may be loaded and inserted into the central channel 36 of the body 34 so that the distal floppy coil 44 protrudes through the valve 38 and out of the body 34 to provide a pacing lead substantially similar in configuration to lead 20 shown in FIG. 2. However, the amount of protrusion can be adjusted to the desired length. Such pacing lead 32 with inserted stylet 42 and coil 44 is steered much the same way as pacing lead 20. It will be appreciated that in both embodiments, the pacing lead or stylet can be coupled to a hemostatic valve coupler such as a rotating hemostatic valve coupler for steering. It will further be appreciated that other guide members such as deflectable members can be used. Placement of the pacing lead is facilitated by use of pre-shaped or shapeable distal end guidewires coupled with the ability to put torque or torsion on the guidewire for positioning. And, while the guidewire may or may not be metallic, the guidewire preferably has a radio-opaque distal tip.

The guidewire is steered into the cardiac veins, thereby leading the way to distal pacing sites. According to the present invention, selective cannulation of the branches of the cardiac veins is conferred by such a guidewire that is curved and rotatably positioned to allow faithful transmission of the torque applied at the proximal end of the stylet by the operator. The floppy design allows the operator to direct and re-direct the coil as needed without the risk of endovascular trauma. Once a vein branch is selected, the coil allows the operator to advance the pacing lead distally, since the coil (and its attached stylet if employed) allows transmission of force along its long axis.

When the coil is in position, the stylet/coil assembly can be withdrawn to leave the pacing lead in position. Note, however, that this embodiment also permits "over the wire" positioning. In other words, the pacing lead can be moved distally over the coil until the distal end of the pacing lead is in any position along the coil. Once in place, the stylet 42 is removed by drawing back through the valve 38 and out of the lead 32. The water-tight valve 38 remains in place and automatically closes to prevent intrusion of blood into the central lumen 36.

Referring more particularly to FIG. 5, the tip portion of the pacing lead 32 with bipolar electrodes 28a, 28b is shown with the pore 40 of water-tight valve 38 closed. Note also that a valve housing 48 is shown. In this closed position, the central channel 40 is sealed as can also be seen in FIG. 6.

Figure 7:
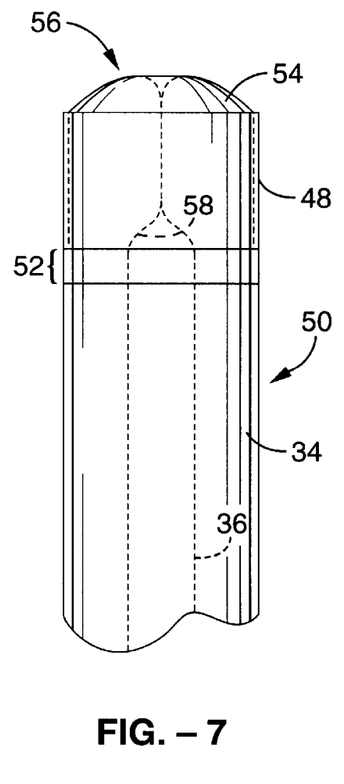
FIG. 7 is a fragmentary view, in side elevation, of an alternative embodiment of the pacing lead of FIG. 3 showing the lead tip having a unipolar electrode configuration and showing a water-light valve having beveled edges in a closed position.

Referring now to FIG. 7, an alternative embodiment of the pacing lead of FIG. 3 through FIG. 6 is shown. Here, the pacing lead 50 has a unipolar electrode 52 and a grommet-type valve 54 with beveled outer 56 and inner 58 edges. Note that the valve 54 is shown in the closed position.

Figure 8:
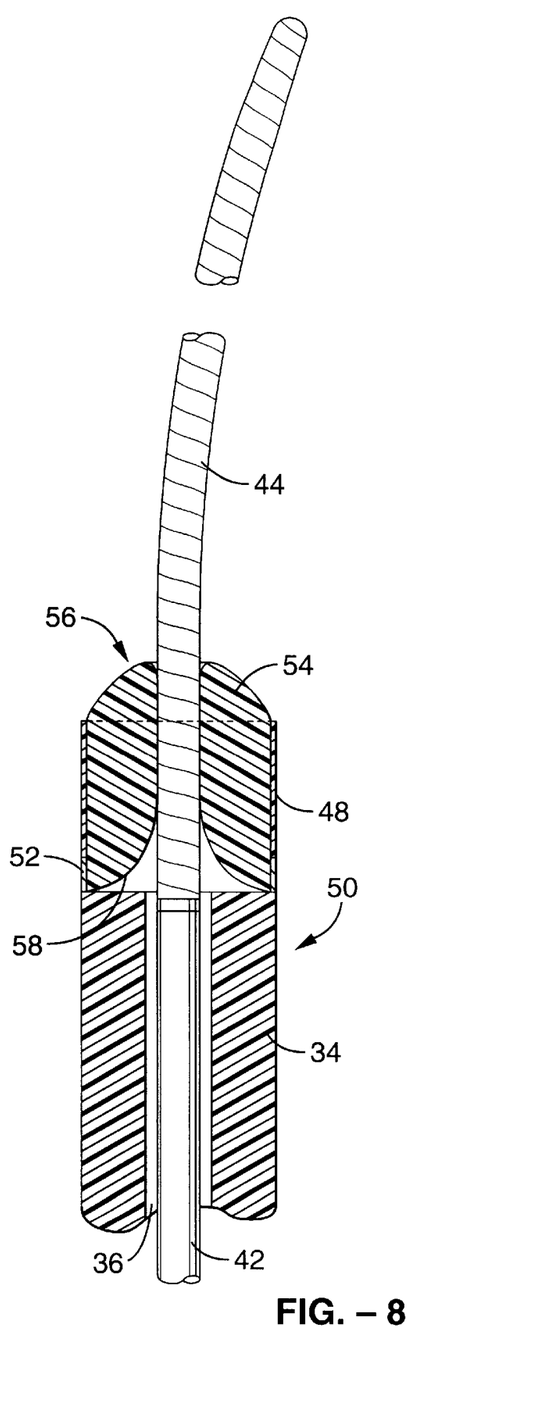
FIG. 8 is a fragmentary cross-sectional view of the lead tip shown in FIG. 7 with the stylet in place and the floppy steerable coil protruding through the pore of the water-tight valve.

When the stylet 42 with attached steerable floppy guidewire 44 is advanced through the central channel 36, the beveled edges of the self-closing valve 54 are pushed forward and out, allowing the stylet 42 with attached steerable floppy guidewire 44 to extrude. The resulting configuration is depicted in FIG. 8 where valve 54 is now in the open position. When the pacing lead 50 has stylet 42 (with attached steerable floppy guidewire 44) inserted therein as depicted in FIG. 8, the surgeon can readily guide the lead into the desired distal vein. Once it is appropriately placed within the patient's heart, the stylet 42 with attached distal floppy coil 44 can be removed, and the valve 54 automatically assumes a closed position.

As indicated previously, conventional lead wires are connected to each of the electrodes and use of lead wires is well known in the art. The lead wires can be manufactured from stainless steel, titanium, cobalt, chromium, silver and non-ferrous alloys. However, titanium and its alloys are preferred, due to acceptable conducting characteristics, flexibility and durability. Insulation surrounds the wire or wires, preventing contact between the wire and the body tissue. The insulation itself is exposed to this tissue, and must therefore be biocompatible. Biocompatability helps to minimize adverse impacts of implanting a foreign object within the body, including such serious events as emboli, thrombi and infection of the cardiovascular system. Pacing lead insulation must be durable, and characterized by an appropriate degree of stiffness. Typically, lead insulation is polyurethane or silicone rubber. Both are relatively biocompatible, and exhibit excellent durability and insulation properties. In one embodiment of the present invention, pacing lead insulation is silicone rubber.

From the foregoing description, it can be seen that the pacing lead of the present invention may be unipolar or bipolar. A unipolar lead has a single distal electrode located at or near the tip of the lead for contact with cardiac tissue. The tip electrode functions as a cathode which transmits the output impulse from the pulse generator to the heart. A bipolar lead, in contrast, has two electrodes, including both a distal tip electrode as well as a proximal ring electrode. It will be appreciated, however, that the tip electrode in a bipolar pacing lead may alternatively be a distal ring electrode, instead of an electrode at the distal tip of the pacing lead. In a bipolar lead, the tip electrode is the contact cathode while the ring electrode is an anode that floats within the heart. In a unipolar lead, the anode is the pulse generator case. The ring electrode is typically located several millimeters proximal to the tip electrode.

Tip electrodes transmit the electrical pulse from the pulse generator to the heart. Those skilled in the art will appreciate that tip electrode design characteristics relevant to lead performance include tip shape, size and porosity. Tips can assume a variety of shapes, and are most commonly hemispherical. The geometric size of a hemispherical tips is determined by the equation $A=2\pi r^2$, without a ring configuration. Tips generally range from approximately 4 mm$^2$ to approximately 12 mm$^2$. In one embodiment of the present invention, the geometric size of the tip electrode is approximately 1 mm². It will also be appreciated that the active surface area of tip of a given geometric size can be increased by forming microscopic ridges and edges, or pores, in the tip surface. It will further be appreciated that electrodes can be made porous and, therefore, the tip electrode of the invention can be made porous to create a larger effective surface area. Increasing surface area of the electrode generally lowers pacing thresholds.

Note also that electrodes, like lead insulation, are exposed to tissue and should be biocompatible. Therefore, biocompatability of the tip electrode is particularly important, as inflammation at the point of contact between the tip electrode and the cardiac tissue may significantly impact the required stimulation voltage. Specifically, collagen encapsulation of the tip electrode may result in radial dispersal of emitted electric field and decrease pacing efficiency. Electrodes can be manufactured of relatively biocompatible material such as titanium and its alloys, platinum and its alloys, iridium, and carbon or metal activated glass. In permanent pacing leads, the corrosion resistance of titanium makes use of this metal particularly desirable. In one embodiment of the present invention, the tip and ring electrodes are titanium. In addition, steroid-eluting electrodes are well known in the art, and can be utilized to further reduce inflammation at the point of contact.

The configuration and pacing lead design of the present invention provides lower capture thresholds in many cases. The low profile pacing lead design and guidewire technology allows the lead to be advanced distally and wedged into a small cardiac vein at distal sites. The thin vascular wall at such sites positions the electrodes in close contact with the epicardial surface. The bipolar pacing lead of the present invention, when configured as a two-ring electrode design (as opposed to the ring and tip leads) assures contact of a large surface area with the epicardial surface. Other data also indicate that electrode design with a low surface area improves capture thresholds in selected cases.

Overall, the insulated wire and electrode comprise a pacing lead that can be shaped or straight. Atrial leads, for example, are often J-shaped. While leads should be able to stretch, this ability is limited and leads are therefore typically selected by length. The appropriate length is determined primarily by the patient's physical characteristics. For example, an average adult pacemaker lead is about 22.0 inches long. As leads are typically permanent, pediatric leads must accommodate considerable growth. Thus, while pediatric leads may be as short as 10.0 inches, excess lead is often positioned within the right atrium.

Figure 9:
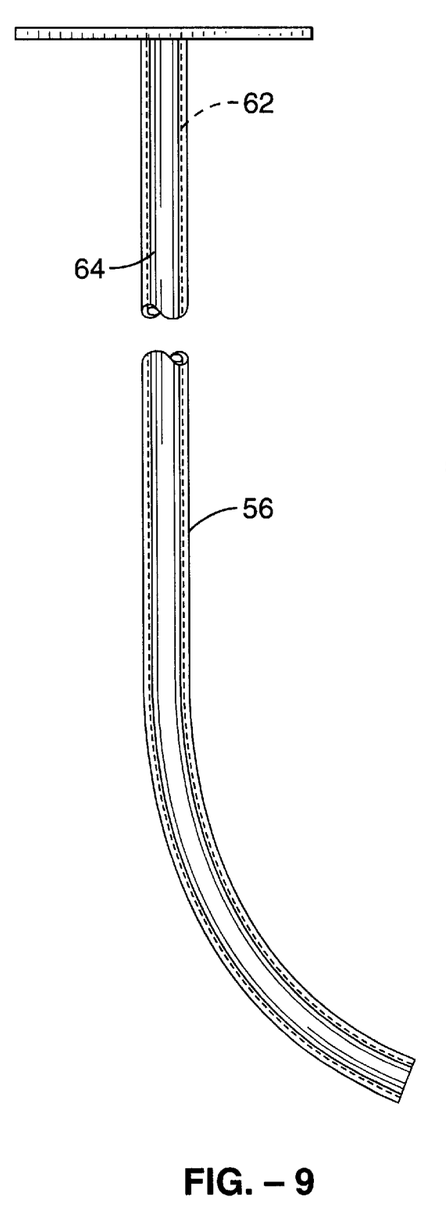
FIG. 9 is a schematic representation of a peel-away sheath portion of a delivery system according to the present invention.
Figures 10, 11:
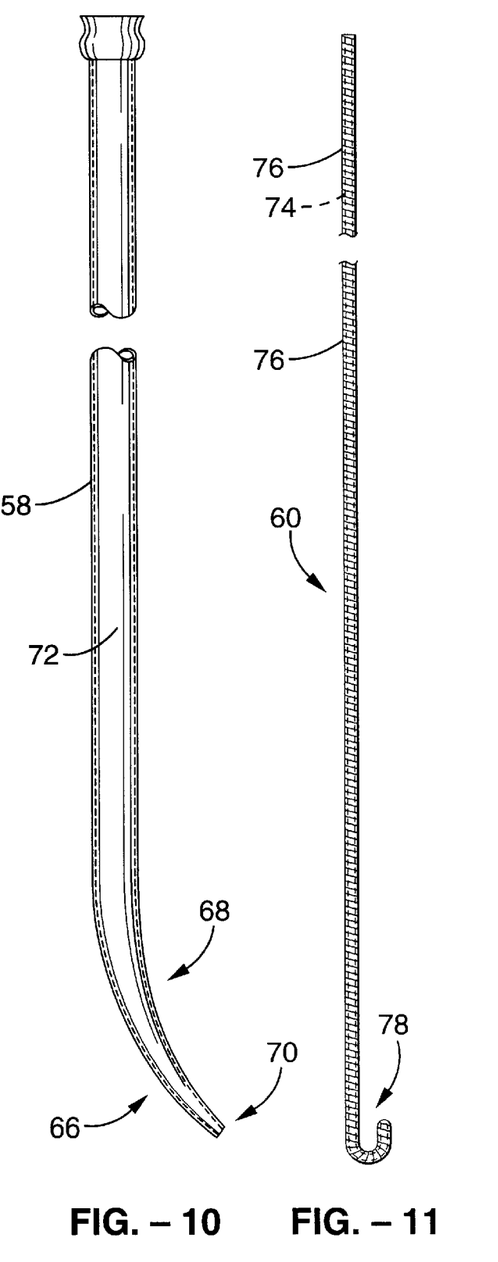
FIG. 10 is a schematic representation of a dilator portion of a delivery system according to the present invention.
FIG. 11 is a schematic representation of a J-tipped guidewire portion of a delivery system according to the present invention.

Referring now to FIG. 9 through FIG. 11, to facilitate use of the present invention we have also developed a delivery system for the pacing lead. The delivery system comprises a sheath 56, a dilator 58, and a J-tipped guidewire 60. The delivery system is used to cannulate the ostium of, for example, the coronary sinus, and to provide guidance for a pacing lead advancable into the coronary sinus.

Conventional pacing leads are delivered to the central circulation with standard sheaths designed for central venous cannulation. In contrast, one embodiment of the delivery system of the present invention incorporates a curved vascular sheath 56 to allow venous access as well as cannulation of the coronary sinus in the inferior right atrial wall. The curved vascular sheath permits the operator to direct the pacing lead into the cardiac veins.

The curved vascular sheath is formed into a preshaped curve allowing cannulation of the coronary sinus. The sheath is typically between approximately 30 cm and approximately 40 cm long, but its length will vary with the size of the patient. For example, pediatric patients need a much shorter sheath. Distally the sheath is molded into a curve of between approximately 45 degrees and approximately 90 degrees. The curve of the distal end of the sheath has typically a radius of curvature of between approximately 6 cm and approximately 8 cm. Alternatively, the curve bends acutely with a distal segment of between approximately 4 cm and approximately 6 cm.

Preferably the curved vascular sheath is formed from a polyethylene blend. The sheath can be made by a process of extrusion, involving melting, stretching, and molding suitable material, such as polyethylene. Tear lines 62 are molded into the sheath, permitting it to be peeled or cut away by methods well known in the art.

The dilator 58 is sized to fit within a central lumen 64 in the sheath and molded into a curve to fit inside the sheath. The distal end 66 of the dilator is formed into a taper 68 and dull tip 70. The dilator has a central lumen 72 to accept the J-tipped wire 60. It is formed, for example, from a polyethylene blend. Dilator 58 can be made by a process of extrusion, involving melting, stretching, and molding suitable material, such as polyethylene.

The J-tipped guidewire 60 comprises an inner monofilament wire 74 surrounded by a coil 76. In one embodiment of the present invention, the diameter of the inner wire 74 is approximately 0.016 inches. The distal portion of the wire is flexible and polished to a smooth hemispherical end. In this embodiment, the coil surrounding the inner wire is approximately 0.006 inches in diameter. The coil is fused to the proximal portion of the inner wire, and shaped into a natural "J" shape at the distal unfused end 78. As a result, the coil bends the inner wire into a similar shape. The inner wire can be straightened by pulling the coil back over the inner wire. In one embodiment of the present invention, both the coil and the inner wire are formed of stainless steel.

In use, the J-tipped guidewire 60 is inserted into the right atrium or right ventricle from a cephalic or subclavian vein. The dilator 58 is positioned within the sheath 56, and the sheath 56 and dilator 58 are advanced over the guidewire 60 into the right ventricle. The guidewire 60 and dilator 58 are then removed, and the sheath 56 is used to cannulate the ostium of the coronary sinus. The sheath 56 then provides a platform for delivery of the pacing lead, as the lead is advanced through the sheath into the coronary sinus. The lead may then be advanced through the sheath into the coronary sinus. The sheath is then pealed or cut away.

EXAMPLE 1

A 60 year old male with recurrent congestive heart failure despite optimal medical therapy, has a left ventricle dilated with reduced function (left ventricular ejection fraction 0.20). An electrocardiogram reveals normal sinus rhythm, first degree atrioventricular block, and left bundle branch block. Catheterization and nuclear imaging data reveal advanced coronary disease, prior myocardial infarctions. There is no anticipated role of bypass surgery or angioplasty. In lieu of a heart transplant, this patient is suitably treated for biventricular pacing.

As can be seen, therefore, a pacing system according to the invention comprises: (1) a pacing lead having a tapering body with a thin distal lead tip portion with at least one electrode; (2) a floppy, steerable coil fixed to the distal end of the pacing lead as a guidewire, or a central channel with a water-tight self-closing grommet-like valve sealing the tip in conjunction with a deformable stylet with a steerable coil bonded to the distal end that is designed to be inserted into the central channel and protrude through the pore of the valve and (3) a long peel-away or cut-away sheath delivery system with a pre-formed curve to facilitate cannulation of, for example, the coronary sinus ostium. In the embodiment having a central lumen running between the proximal and distal ports and a self-closing valve at the distal tip, the guidewire can be inserted and removed for initial placement of the pacing lead and later readjustment of position if necessary. The self-closing valve prevents leakage and potential blood clotting in the central lumen.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A cardiac pacing lead, comprising:
    a tapered body having a thin distal end relative to its proximal end;
    at least one electrode attached to said tapered body adjacent said distal end;
    a lumen within the tapered body alolig the distal end portion; and
    a valve located on the distal end of the tapered body and adapted to allow a guide member to be slideably advanced through the valve and also to provide a substantial fluid seal to the lumen at the valve.

2. A cardiac pacing lead as recited in claim 1, further comprising a guidewire that is adapted to couple to said tapered body within said lumen at said distal end.

3. A cardiac pacing lead as recited in claim 2, wherein said guldewire comprises a distal end having a floppy coil.

4. A cardiac pacing lead as recited in claim 3, wherein said distal end with said floppy coil is steerable.

5. A cardiac pacing lead as recited in claim 1, wherein said tapered body includes proximal and distal ports, and said lumen extends between said proximal and distal ports.

6. A cardiac pacing lead as recited in claim 1, wherein said valve comprises a self-closing port coaxially aligned with said distal port.

7. A cardiac pacing lead as recited in claim 1, further comprising a guide member that is insertable through said lumen and said valve.

8. A cardiac pacing lead as recited in claim 7, wherein said guide member comprises a guidewire with a distal end gortion having a floppy coil.

9. A cardiac pacing lead as recited in claim 8, wherein said distal end portion with said floppy coil is steerable.

10. A cardiac pacing lead as recited in claim 8, wherein said floppy coil is steerable.

11. A cardiac pacing lead as recited in claim 1, wherein said distal end portion of said body has a diameter between approximately 1 mm and 3 mm.

12. A cardiac pacing lead, comprising:
    a tapered body having a thin distal end relative to its proximal end;
    at least one electrode attached to said tapered body adjacent said distal end;
    a guidewire attached to said tapered body at said distal end; and
    a stylet lumen within the tapered body that is adapted to receive a stylet.

13. A cardiac pacing lead as recited in claim 12, wherein said guidewire comprises a distal end portion with a floppy coil.

14. A cardiac pacing lead as recited in claim 13, wherein said distal end portion with said floppy coil is steerable.

15. A cardiac pacing lead as recited in claim 12, wherein said distal end of said body has a diameter between approximately 1 mm and 3 mm.

16. A cardiac pacing lead, comprising:
    (a) a tapered body having proximal and distal ends, proximal and distal ports, and a lumen extending between said ports, said distal end of said body being thin relative to said proximal end;
    (b) at least one electrode attached to said tapered body adjacent said distal end; and
    (c) a valve attached at said distal end of said body, said valve having a self-closing port coaxially aligned with said distal port.

17. A cardiac pacing lead as recited in claim 16, further comprising a guidewire that is insertable through said lumen and said valve.

18. A cardiac pacing lead as recited in claim 17, wherein said guidewire comprises a floppy coil.

19. A cardiac pacing lead as recited in claim 18, wherein sid floppy coil is steerable.

20. A cardiac pacing lead as recited in claim 16, wherein said distal end of said body has a diameter between approximately 1 mm and 3 mm.

21. A cardiac pacing device for left ventdcular pacing via the distal cardiac veins, comprising:
    a tapering body with a thin distal lead shaft of between about 1 mm and about 3 mm in diameter;
    at least one electrode attached to the tapering body, the electrode providing low rapture thresholds;
        means for tracking the tapering body over a quidewire into the distal cardiac veins;
        means for providing a substantial seal against fluid ingress into the tapering body within the distal cardiac veins; and
    wherein the device lacks attachment means for securing the distal end to the wall of the heart after placement.

22. A cardiac pacing device as recited in claim 21, wherein:
    the means for tracking comprises a central channel through the tapering body;
    the means for providing the substantial seal a water-tight grommet valve closeable to seal the tip, said valve having a pore continuous with said central channel when said valve is open.

23. A cardiac pacing device as recited in claim 22, further comprising a guide member that is insertable into and through the central channel of the tapering body, to protrude through the pore of the valve.

24. A cardiac pacing device as recited in claim 21, wherein said guide member further comprises a steerable guidewire.

25. A cardiac pacing device for left ventricular padng via the distal cardiac veins, comprising:
    a tapering body with a thin distal lead shaft of between about 1 mm and about 3 mm in diameter;
    at least one electrode attached to the taperng body, the electrode providing low capture thresholds; and
    a distal steerable guldewire fixed to the distal end of the device;
    wherein the device lacks attachment means for securing the distal end to the wall of the heart after placement.

26. A cardiac pacing lead, comprising:
    a tapered body having a thin distal end relative to its proximal end, proximal and distal ports, and a lumen extending between said proximal and distal ports;

at least one electrode attached to said tapered body adjacent said distal end; and a valve attached at said distal end of said body and having a self-closing port coaxially aligned with said distal port.

27. A cardiac pacing lead as recited in claim 26, further comprising a guidewire that is insertable through said lumen and said valve.

28. A cardiac pacing lead as recited in claim 27, wherein said guidewire comprises a floppy coil.

29. A cardiac pacing device for left ventricular pacing via the distal cardiac veins, comprising:

a tapering body with a thin distal lead shaft of between about 1 mm and about 3 mm in diameter;

at least one electrode attached to the tapering body, the electrode providing low capture thresholds;

a central channel through the tapering body; and a water-tight grommet valve closeable to seal the tip, said valve having a pore continuous with said central channel when said valve is open;

wherein the device lacks attachment means for securing the distal end to the wall of the heart after placement.

30. A cardiac pacing device as recited in claim 29, further comprising a guide member that is insertable into and through the central channel of the tapering body to protrude through the pore of the valve.

* * * * *